United States Patent
Somani et al.

(10) Patent No.: US 7,238,177 B2
(45) Date of Patent: *Jul. 3, 2007

(54) METHODS AND SYSTEMS FOR LASER CALIBRATION AND EYE TRACKER CAMERA ALIGNMENT

(75) Inventors: Seema Somani, Milpitas, CA (US); Kingman Yee, San Jose, CA (US); John K. Shimmick, Belmont, CA (US)

(73) Assignee: Visx, Incorporated, Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/264,785

(22) Filed: Oct. 31, 2005

(65) Prior Publication Data

US 2006/0103839 A1    May 18, 2006

Related U.S. Application Data

(60) Division of application No. 10/685,253, filed on Oct. 13, 2003, now Pat. No. 7,001,376, which is a division of application No. 10/131,622, filed on Apr. 23, 2002, now Pat. No. 6,666,855, which is a continuation-in-part of application No. 09/395,809, filed on Sep. 14, 1999, now Pat. No. 6,559,934.

(51) Int. Cl.
*A61F 9/01* (2006.01)
(52) U.S. Cl. .............................. 606/5; 606/4; 128/898
(58) Field of Classification Search ........ 356/121–127, 356/243.1–243.8, 252.1, 252.2; 606/4, 5, 606/12, 10, 13; 372/22, 23; 128/898
See application file for complete search history.

(56) References Cited

U.S. PATENT DOCUMENTS 3,572,889 A * 3/1971 Bloomfield .................. 359/390

(Continued)

FOREIGN PATENT DOCUMENTS

JP         59225320 A1    12/1984

(Continued)

OTHER PUBLICATIONS

Borsutzky, et al.; "Tunable UV Radiation at Short Wavelengths (188-240 nm) Generated by Sum-Frequency Mixing in Lithium Borate;" *Appl. Phys. B 52:* 1991; pp. 380-384.

*Primary Examiner*—Hoa Q. Pham
(74) *Attorney, Agent, or Firm*—Townsend & Townsend & Crew LLP; Mark D. Barrish

(57) ABSTRACT

The present invention provides methods, systems, and apparatus for calibrating a laser ablation system, such as an excimer laser system for selectively ablating a cornea of a patient's eye. The invention also facilitates alignment of eye tracking cameras that measure a position of the eye during laser eye surgery. A calibration and alignment fixture for a scanning laser beam delivery system having eye tracking cameras may include a structure positionable in a treatment plane. The structure having a feature directing laser energy incident thereon to a calibration energy sensor, at least one reference-edge to determine a characteristic of the laser beam (shape, dimensions, etc.), and an artificial pupil to determine alignment of the eye tracking cameras with the laser system.

11 Claims, 14 Drawing Sheets

U.S. PATENT DOCUMENTS

| | | |
|---|---|---|
| 4,713,537 A | 12/1987 | Kunz et al. |
| 4,848,902 A | 7/1989 | Schickle et al. |
| 5,031,203 A | 7/1991 | Trecha |
| 5,059,021 A | 10/1991 | Spence et al. |
| 5,078,491 A | 1/1992 | Johnston, Jr. |
| 5,137,363 A * | 8/1992 | Kosugi et al. ............... 356/401 |
| 5,144,630 A | 9/1992 | Lin |
| 5,267,012 A | 11/1993 | Sasnett et al. |
| 5,424,538 A | 6/1995 | Yoshino |
| 5,446,548 A | 8/1995 | Gerig et al. |
| 5,459,565 A | 10/1995 | Aharon |
| 5,694,209 A | 12/1997 | Alfille et al. |
| 5,742,626 A | 4/1998 | Mead et al. |
| 5,772,656 A | 6/1998 | Klopotek |
| 5,782,822 A | 7/1998 | Telfair et al. |
| 5,843,070 A | 12/1998 | Cambier et al. |
| 5,909,274 A | 6/1999 | Stucchi |
| 5,928,221 A | 7/1999 | Sasnett et al. |
| 5,936,728 A * | 8/1999 | Bouzid ....................... 356/318 |
| 5,999,550 A | 12/1999 | Bellemore et al. |
| 6,090,102 A | 7/2000 | Telfair et al. |
| 6,138,503 A | 10/2000 | Ray |
| 6,195,164 B1 | 2/2001 | Thompson et al. |
| 6,322,216 B1 | 11/2001 | Yee et al. |
| 6,322,555 B1 | 11/2001 | LaHaye |
| 6,331,177 B1 | 12/2001 | Munnerlyn et al. |
| 6,535,282 B2 | 3/2003 | Hedges et al. |
| 6,559,934 B1 | 5/2003 | Yee et al. |
| 6,666,855 B2 | 12/2003 | Yee et al. |
| 6,817,998 B2 | 11/2004 | LaHaye |
| 7,001,375 B2 * | 2/2006 | Yee et al. ...................... 606/5 |
| 7,001,376 B2 | 2/2006 | Somani et al. |
| 2003/0225399 A1 | 12/2003 | Chernyak et al. |

FOREIGN PATENT DOCUMENTS

| | | |
|---|---|---|
| WO | WO 99/42885 A1 | 8/1999 |
| WO | WO 02/76319 A1 | 3/2002 |

\* cited by examiner

METHODS AND SYSTEMS FOR LASER CALIBRATION AND EYE TRACKER CAMERA ALIGNMENT

CROSS-REFERENCES TO RELATED APPLICATIONS

This application is a divisional of and claims the benefit of priority from U.S. patent application Ser. No. 10/685,253, filed Oct. 13, 2003, now U.S. Pat. No. 7,001,376, which is a divisional of and claims the benefit of priority from U.S. patent application Ser. No. 10/131,622, filed Apr. 23, 2002, now U.S. Pat. No. 6,666,855, which is a continuation-in-part of and claims the benefit of priority from U.S. patent application Ser. No. 09/395,809, filed Sep. 14, 1999, now U.S. Pat. No. 6,559,934, the full disclosures of which are incorporated herein by reference.

BACKGROUND OF THE INVENTION

The present invention is generally directed to methods, systems, and apparatus for laser calibration and eye tracker camera alignment. In particular, the present invention relates to methods and systems for measuring laser energy, shape, and dimensions of a laser beam from a laser beam delivery system, particularly opthalmological surgery systems, and aligning eye tracking cameras used in conjunction with such laser systems that measure a position of the eye during laser eye surgery.

Laser-based systems are now used in opthalmological surgery on corneal tissues to correct vision defects. These systems use lasers to achieve a desired change in corneal shape, with the laser removing thin layers of corneal tissue using a technique generally described as ablative photodecomposition to alter the cornea's refractive power. Laser eye surgery techniques are useful in procedures such as photorefractive keratotomy (PRK), phototherapeutic keratectomy (PTK), laser in situ keratomileusis (LASIK), and the like.

In such laser-based systems and methods, the irradiated flux density and exposure time of the cornea to the laser radiation are controlled so as to provide a surface sculpting of the cornea to achieve a desired ultimate surface change in the cornea. To that end, ablation algorithms have been developed that determine the approximate energy density that must be applied to remove a certain depth of tissue from the cornea. At ultraviolet wavelengths, for example, a cumulative energy density of about 1 joule/cm$^2$ will typically ablate corneal tissue to a depth of about one micron when applied in a series of pulses of about 40 to 400 millijoules/cm$^2$. Accordingly, the ablation algorithms are tailored for each procedure depending on the amount and the shape of corneal tissue which will be removed to correct a particular individual's refractive error.

In order to properly use these laser ablation algorithms, the laser beam delivery system typically should be calibrated. Calibration of the laser system helps ensure removal of the intended shape and quantity of the corneal tissue so as to provide the desired shape and refractive power modification to the patient's cornea. For example, deviation from a desired laser beam shape or size, such as the laser beam exhibiting a non-symmetrical shape or an increased or decreased laser beam diameter, may result in tissue ablation at an undesired location on the patient's cornea which in turn leads to less than ideal corneal sculpting results. As such, it is beneficial to know the shape and size profiles of the laser beam so as to accurately sculpt the patient's cornea through laser ablation. In addition, it is usually desirable to test for acceptable levels of system performance. For example, such tests can help ensure that laser energy measurements are accurate. Ablations of plastic test materials are often performed prior to laser surgery to calibrate the laser energy and ablation shape of the laser beam delivery system. Although such laser ablation calibration techniques are fairly effective, in some instances, alternative methods for laser energy and beam shape calibration may be advantageous.

A variety of integrated structures have been proposed for both scanning of a laser beam across the corneal tissue and tracking of eye movements. Tracking of the eye during laser eye surgery has been proposed to avoid uncomfortable structures which attempt to achieve total immobilization of the eye. Tracking further compensates for eye movement during a treatment procedure so that the intended portion of the eye may be accurately ablated. An exemplary two camera off-axis eye tracker for laser eye surgery is described in U.S. Pat. No. 6,322,216 B1, assigned to the assignee of the present application, the full disclosure of which is incorporated herein by reference. In this system, first and second cameras or image capture devices are oriented toward the eye. An energy delivery system laterally deflects an energy stream toward the corneal tissue along a first and second axis in response to movement of the eye sensed by the first and second image capture devices. Alignment of such image capture devices may be facilitated by a jig plate.

In light of the above, it would be desirable to provide improved methods, systems, and apparatus for calibrating laser energy, laser beam shape, and/or laser beam dimensions from a laser eye surgery system. It would be particularly desirable if such improvements enhanced calibration accuracy without significantly increasing the overall system cost and complexity. It would be further desirable if such methods, systems, and apparatus further allow for eye tracker camera alignment so that laser calibration and camera alignment may be conveniently and effectively carried out utilizing a single, reusable apparatus. At least some of these objectives will be met by the methods, systems, and apparatus of the present invention described hereinafter.

BRIEF SUMMARY OF THE INVENTION

The present invention provides methods, systems, and apparatus for calibrating a laser ablation system, such as an excimer laser system for selectively ablating a cornea of a patient's eye. The invention also facilitates alignment of eye tracking cameras (which are often used in conjunction with such laser systems) that measure a position of the eye during laser eye surgery. In particular, the present invention provides methods and systems which measure laser energy, laser beam shape, and/or laser beam dimensions with enhanced calibration accuracy without significantly increasing the overall system cost and complexity. Moreover, the present invention allows for laser calibrations and eye tracker camera alignment to be effectively and conveniently carried out.

In a first aspect of the present invention, a method for calibrating laser energy from a laser eye surgery system comprises transmitting or reflecting a laser beam suitable for ablation of corneal tissue from a surface, such as a galvanometric mirror having a reflecting surface or a beam splitter, and scanning the laser beam across a calibration fixture having a feature, such as an opening, reference-edge, or artificial pupil. Sample laser energy is separated from the beam at the surface during the scanning and measured. Laser energy transmitted past or directed at the feature during the scanning is measured. A calibration of the laser system is then determined by comparing the energy measurements. Energy measurements during the scanning are typically made by energy sensors, such as a photodetectors, light detectors, energy meters, and like detectors that are positioned near, adjacent to, or behind the surface or calibration fixture.

Calibration of the laser system is determined by comparing a ratio of the measured sample laser energy and the measured laser energy directed at the feature to a predetermined tolerance. If the ratio is within the predetermined tolerance, calibration of the laser system further comprises independently comparing the measured sample laser energy to a first threshold range and the measured laser energy directed at the feature to a second threshold range. Calibration of the laser system is complete if the measured sample laser energy is within the first threshold range and the measured laser energy directed at the feature is within the second threshold range. In a passing calibration, the calibration fixture may then be removed from a treatment plane and the laser beam directed towards a patient's cornea for ablating the cornea with the calibrated system. However, if the measured sample laser energy is outside the first threshold range or the measured laser energy directed at the feature is outside the second threshold range, a fault is indicated in the laser system, such as flawed delivery system optics or a flawed laser.

The laser beam may be transmitted from several different positions on the surface. In the case where the ratio is outside the predetermined tolerance, each ratio of the measured sample laser energy and the measured laser energy directed at the feature is analyzed for each laser beam position on the surface to determine if the ratio is position independent. If the ratio is not position independent, a fault is indicated either in the surface or an energy sensor that measures sample energy or laser energy directed at the feature. If the ratio is position independent, a fault is indicated either in the energy sensor that measures sample energy or laser energy directed at the feature or the laser beam delivery system. Calibration of the laser system may further indicate if an energy sensor measures the sample energy or laser energy directed at the feature at an accuracy within a predetermined threshold.

As described above, the surface preferably comprises a mirror having a reflecting surface, wherein a photodetector measures sample energy, such as laser energy leakage through the mirror. The feature comprises an opening in the calibration fixture which is positioned adjacent a treatment plane, wherein a photodetector measures laser light energy passing through the opening. A variation in each photodetector due to spatial non-uniformity is further measured prior to laser beam scanning across the calibration fixture to separate this effect from the laser energy calibration calculations described above. Moreover, a large number of measurements are made so that contributions due to detector noise are relatively insignificant as compared to an average of laser energy measurements. The tolerance and threshold values will depend on the level of calibration accuracy desired. For example, the predetermined ratio tolerance provides preferably 8% or less inaccuracy, more preferably 4% or less inaccuracy, most preferably 2% or less inaccuracy while the threshold values may provide 1% or less inaccuracy. The laser beam will typically be oriented perpendicular to the calibration fixture. The present methods advantageously allow for enhanced laser energy calibration as energy measurements from two photodetectors are used to determine an accurate calibration of the laser system. Moreover, energy measurements from two photodetectors allow for fault detection within the laser system to be narrowed to a specific source(s), which in turn facilitates fast and accurate adjustment of the laser system.

The calibration feature may further comprise a first reference-edge, such as a knife-edge, so as to determine a characteristic of the laser beam by measuring laser energy passing the first reference-edge during scanning with a photodetector. Multiple measurements are generated as the laser beam is fully incident on the first reference-edge (i.e. the laser beam is fully blocked from reaching the photodetector by the reference-edge) to the laser beam being fully incident on the photodetector (i.e. the laser beam is not blocked by the reference-edge). The calibration feature will preferably comprise a second reference-edge oriented at an angle relative to the first reference-edge. A characteristic of the laser beam may be determined by measuring laser energy passing the second reference-edge during scanning.

An intensity profile of the laser beam may be determined from the measured laser energy passing the first or second reference-edges during scanning. The scanning laser beam provides an integration of the laser beam intensity profile. Dimensions of the laser beam may then be determined from the laser beam intensity profile. For example, dimensions of the laser beam may be determined by finding positions of the laser beam along the two orthogonal reference-edges where the measured laser energy passing the reference-edge during the scanning reaches a certain percent of a maximum signal. In some instances, the intensity profile of the laser beam may be verified so that it is within a predetermined acceptable range from the compared energies. A shape of the laser beam may further be determined by measuring a rate of change of the measured laser energy passing the reference-edge during scanning. Laser beam shape and dimension measurements provide information on beam quality, such as ellipticity, eccentricities, and asymmetries in the laser beam, which in turn facilitates accurate sculpting of the cornea.

The calibration feature may further be imaged with an image capture device of an eye tracker system so as to align the image capture device with the laser system. In such instances, the calibration feature may comprise four dark circles that preferably emulate eye pupils disposed at four corners of a square. Alternatively or additionally, the imaged feature may comprise an opening or a reference-edge.

In another aspect of the present invention, methods for characterizing a scanning corneal ablation laser beam are provided. One method comprises scanning a laser beam across a calibration fixture having a reference-edge, measuring the laser beam energy passing the reference-edge while scanning the laser beam, and deriving a characteristic of the laser beam from the measured laser beam energy. The calibration fixture may be removed following measurement and the a patient's eye treated by ablating the patient's cornea with the measured laser beam.

In yet another aspect of the present invention, systems for calibrating laser energy from a laser beam delivery system are provided. Such systems may comprise a scanning laser beam delivery system, preferably a laser eye surgery system, a surface that directs laser energy from the laser beam delivery system toward a treatment plane, the surface separating a sample laser energy from the beam, a first photodetector positioned in a first optical path of the sample laser energy from the surface, a calibration fixture positioned adjacent the treatment plane, and a second photodetector positioned in a second optical path of the laser beam from the feature of the calibration fixture. The first photodetector emits a first output signal in response to the sample laser energy, for example, the amount of laser energy leakage through the surface or mirror. The second photodetector emits a second output signal in response to the laser beam incident thereon. A processor is also included in the system to determine a calibration of the laser system or a characteristic of the laser beam in response to the first and second output signals.

The calibration feature may comprise an opening in the calibration fixture that is sufficiently large so that a whole of the laser beam can pass through it. The calibration feature may further comprise a reference-edge or two reference-edges so that the laser beam is directed from the surface across each reference-edge so as to determine a characteristic of the laser beam (e.g., shape, dimension). In an exemplary embodiment, the calibration feature has a cross-like pattern comprising twelve reference-edges so as to allow for multiple measurements which in turn enhances laser beam dimension and shape measurements. The system may further comprise an image capture device orientated toward the treatment plane and an image processor coupled to the image capture device. The image processor determines a position of the calibration fixture for verification of alignment between the image capture device and the laser delivery system. In such instances, the imaged calibration feature preferably comprises four dark circles disposed at four corners of a square pattern.

In a still further aspect of the present invention, a calibration and alignment fixture for a scanning laser beam delivery system having at least one image capture device may comprise a structure positionable in a treatment plane. The structure has a feature directing laser energy incident thereon to a calibration energy sensor, at least one reference-edge to determine a characteristic of the laser beam (e.g., shape, dimension), and an artificial pupil to determine alignment of the at least one image capture device with the laser system. The calibration feature comprises an opening that is sufficiently large so that a whole of the laser beam can pass through it. Preferably, the calibration fixture has two reference-edges, the second reference-edge oriented at an angle relative to the first reference-edge, more preferably the fixture has a cross-like pattern comprising twelve reference-edges. The artificial pupil may comprise a dark circle, preferably four dark circles disposed at four corners of a square, or an opening or hole in the fixture. The cross-like pattern of twelve reference-edges may also be used to align the image capture device with the laser system. Conveniently, laser calibration and laser beam characteristics may be determined and eye tracking cameras aligned effectively via a single, reusable fixture.

In another aspect of the present invention, a method for calibrating a laser eye surgery system having eye tracking cameras is provided. A position of a laser beam is measured, a position of a calibration feature is measured, and the measured position of the laser beam is compared to the measured position of the calibration feature. If the measured positions are within a predetermined tolerance, the eye may be treated via corneal ablation.

A further understanding of the nature and advantages of the present invention will become apparent by reference to the remaining portions of the specification and drawings.

DETAILED DESCRIPTION OF THE INVENTION

The present invention provides methods, systems, and apparatus for calibrating a laser ablation system, such as an excimer laser system for selectively ablating a cornea of a patient's eye. The present invention also facilitates aligning eye tracking cameras that measure a position of the eye during laser eye surgery. In particular, the present invention provides methods and systems which measure laser energy, laser beam shape, and/or laser beam dimensions with enhanced calibration accuracy. By determining an exact quality of a laser beam, a desired corneal ablation treatment can be accurately effected via an ablation algorithm without underablating or overablating corneal tissue, or the laser beam becoming incident on undesired locations of corneal tissue causing off-center ablations. Moreover, embodiments of the present invention allow for laser beam calibration and eye tracker camera alignment to be simply and conveniently carried out utilizing a single, reusable fixture.

Figure 1:
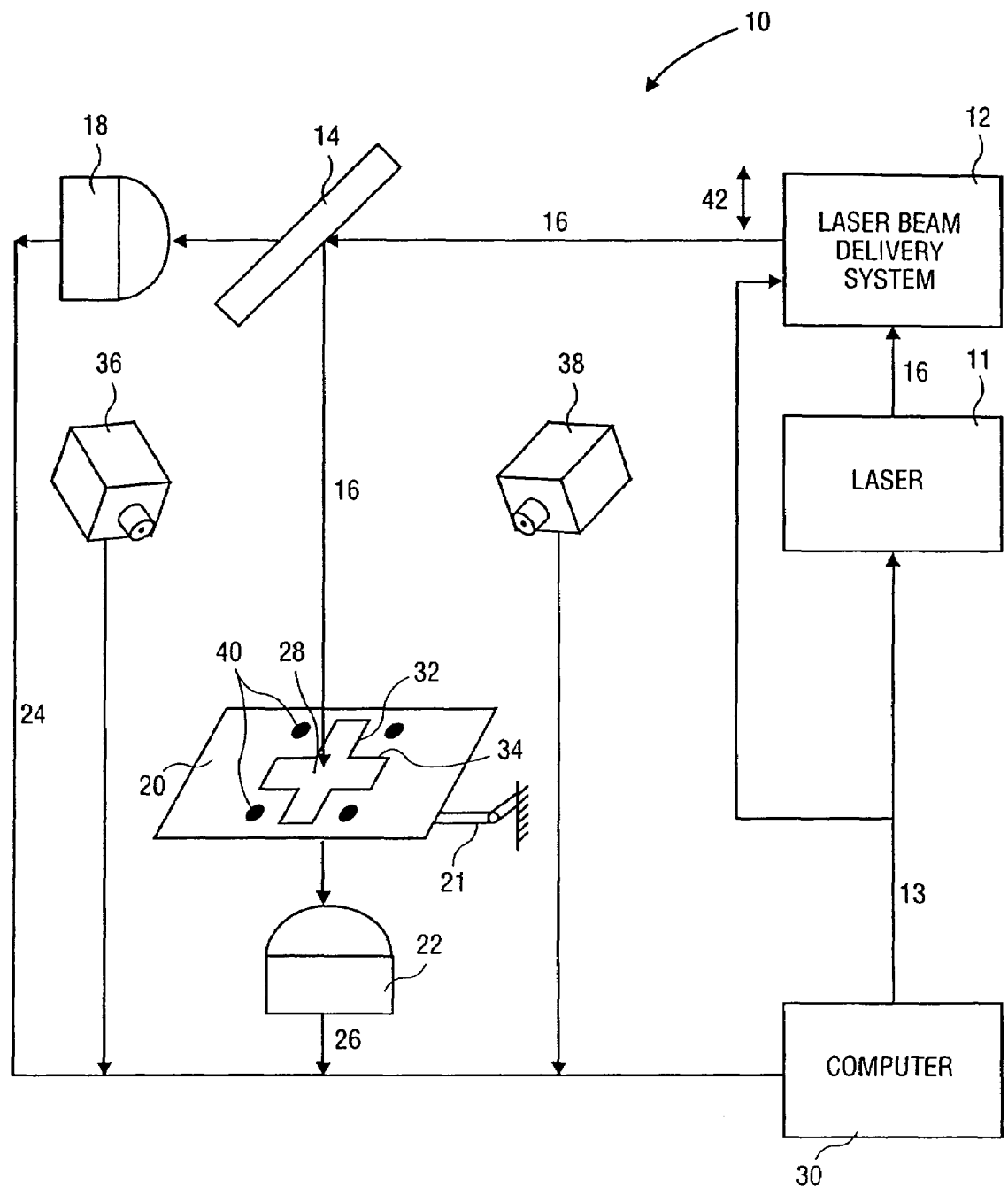
FIG. 1 illustrates a schematic of a system for laser calibration and eye tracker camera alignment constructed in accordance with the principles of the present invention.

Referring now to FIG. 1, an exemplary calibration system 10 constructed in accordance with the principles of the present invention for calibrating laser energy and aligning eye tracking cameras is schematically illustrated. System 10 is particularly useful for calibrating and aligning a laser ablation system of the type used to ablate a region of the cornea in a surgical procedure, such as an excimer laser used in photorefractive keratotomy (PRK), phototherapeutic keratectomy (PTK), laser in situ keratomileusis (LASIK), and the like. Such systems 10 generally comprise a laser 11, a scanning laser beam delivery system 12, a surface, such as, a mirror 14 having a reflecting surface that directs laser energy 16 from the laser beam delivery system 12 toward a treatment plane, a first photodetector 18 positioned behind the mirror 14, a calibration fixture 20 positioned near or adjacent the treatment plane, and a second photodetector 22 positioned behind the calibration fixture 20. The first photodetector 18 provides a first output signal 24 in response to sample laser energy separated from the beam at the surface, in this instance, the amount of laser energy leakage through the mirror 14. The second photodetector 22 provides a second output signal 26 in response to laser beam incident thereon and passing by a feature, such as a feature formed in an opening 28, in the calibration fixture 20. A computer system 30 is also included in the system 10 to record, process, and analyze the first and second output signals 24 and 26 to determine a calibration of the laser system or a characteristic of the laser beam. The computer 30 may also provide signals 13 for controlling the laser 11 and laser beam delivery system 12. Computer system 30 generally includes a processor, tangible media for storing instructions, random access memory, and other storage media like hard and floppy drives. It will be appreciated that the following depictions are for illustration purposes only and does not necessarily reflect the actual shape, size, or dimensions of the integrated calibration and alignment system 10. This applies to all depictions hereinafter.

The laser beam delivery system 12 may include, but is not limited to, an excimer laser such as an argon-fluoride excimer laser producing laser energy with a wavelength of about 193 nm. Alternative laser systems may include solid state lasers, such as frequency multiplied solid state lasers, flash-lamp and diode pumped solid state lasers, and the like. Exemplary solid state lasers include UV solid state lasers producing wavelengths of approximately 188–240 nm such as those disclosed in U.S. Pat. Nos. 5,144,630, and 5,742, 626; and in Borsuztky et al., *Tunable UV Radiation at Short Wavelengths* (188–240 nm) *Generated by Frequency Mixing in Lithium Borate, Appl. Phys.* 61:529–532 (1995), the full disclosures of which are incorporated herein by reference. A variety of alternative lasers might also be used. For example, a pulsed solid state laser emitting infrared light energy may be used as described in U.S. Pat. Nos. 6,090,102 and 5,782,822, the full disclosures of which are incorporated herein by reference. The laser energy generally comprises a beam formed as a series of discrete laser pulses, and the pulses may be separated into a plurality of beamlets as described in U.S. Pat. No. 6,331,177, the full disclosure of which is incorporated herein by reference.

The calibration fixture opening 28 is sufficiently large so that a whole of the laser beam can pass through it. The calibration fixture 20 further comprises two reference-edges 32, 34 so that the laser beam is directed from the mirror 14 across each reference-edge having the second photodetector 22 positioned therebehind so as to determine a characteristic of the laser beam (e.g., shape, dimension). In the exemplary embodiment shown, the calibration fixture 20 has a cross-like pattern comprising twelve reference-edges so as to allow for multiple measurements which in turn enhances laser beam dimension and shape measurements. The system 10 may further comprise first and second cameras or image capture devices 36 and 38 orientated toward the treatment plane to track a position of an eye. In such instances, the calibration fixture 20 further comprises four dark circles 40 that preferably emulate eye pupils disposed at four corners of a square pattern so as to facilitate alignment of the cameras 36 and 38 with the laser system.

Figure 2:
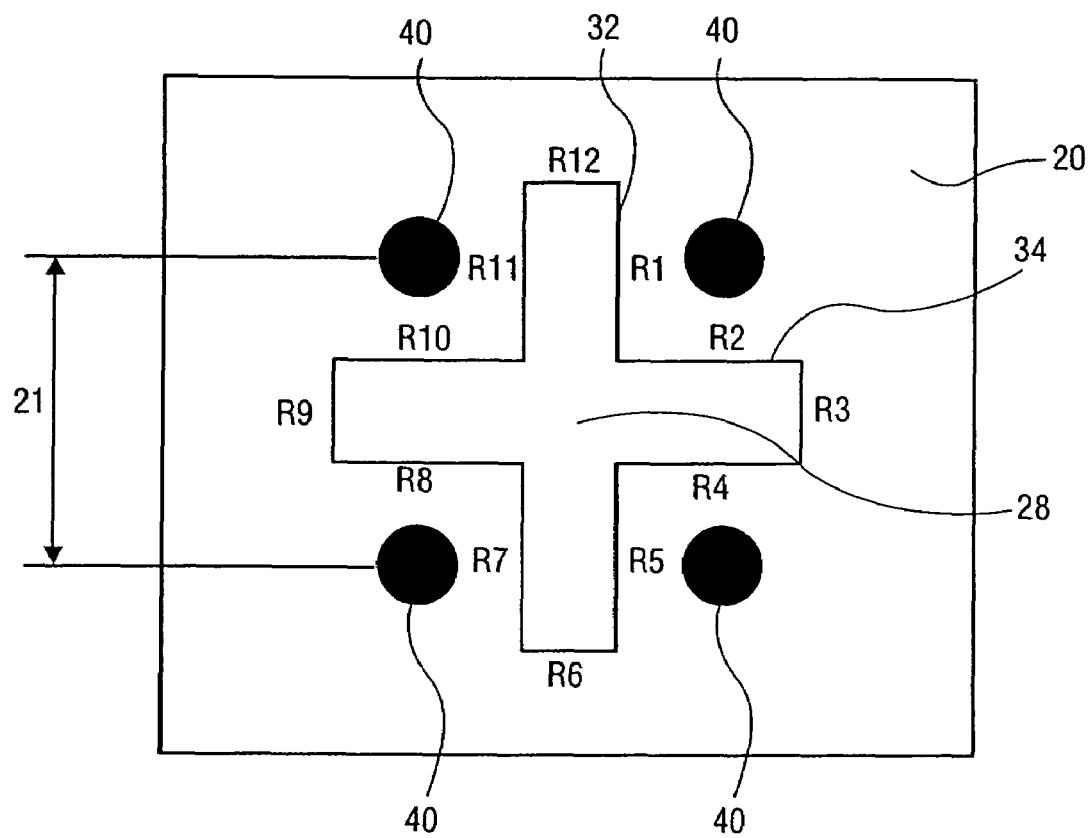
FIG. 2 illustrates an exploded view of the calibration and alignment fixture employed in the system of FIG. 1.

Referring now to FIG. 2, an exploded view of the exemplary calibration and alignment fixture 20 employed in the system 10 of FIG. 1 is illustrated. The fixture 20 comprises a structure positionable in a treatment plane. The structure 20 generally comprises a flat sided body having a credit card structure which has a width in the range from 10 mm to 50 mm, a length in the range from 10 mm to 50 mm, and a thickness in the range from 0.1 mm to 5 mm. The structure 20 may be formed from a variety of materials, including metal, steel, silicon, crystals, or like materials. The structure 20 has an opening 28, groove, notch, or slit to allow for laser energy calibration, at least one reference-edge, preferably two reference-edges 32, 34 that are oriented perpendicular to each other so as to determine a characteristic of the laser beam, and an artificial pupil, preferably four dark circles 40 that are disposed at four corners of a square pattern so as to determine an optical center and rotational alignment of eye tracking cameras. The calibration fixture opening 28 is preferably centered within the structure 20. In the exemplary embodiment, the calibration fixture forms a cross-like pattern comprising twelve reference-edges, preferably knife-edges, which are referenced as R1 through R12 in FIG. 2. The reference-edges are generally oriented perpendicular to one another and have a length in the range from 1 mm to 10 mm. The dark circles 40 disposed on the fixture 20 will typically have a diameter in the range from 0.25 mm to 2 mm, and be formed from a variety of materials, including metals, steel, silicon, or like materials. The alignment circles 40 will be sufficiently placed away from the reference-edges R1 through R12, with the square having side lengths 21 of about 14 mm. It will be appreciated that the artificial pupil may also comprise an opening or hole in the calibration fixture. Conveniently, laser energy calibration and laser beam characteristics may be determined and eye tracking cameras aligned effectively utilizing this single, reusable fixture 20, as described in greater detail below.

Figure 2A:
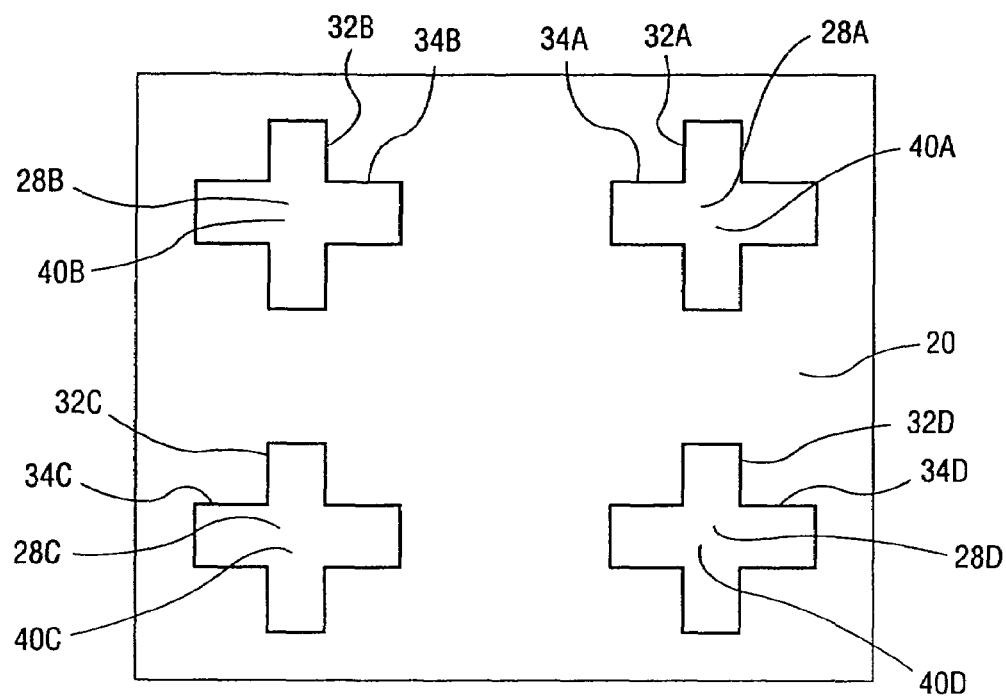
FIGS. 2A and 2B illustrate alternative configurations of the calibration and alignment fixture which may be employed in the system of FIG. 1.
Figure 2B:
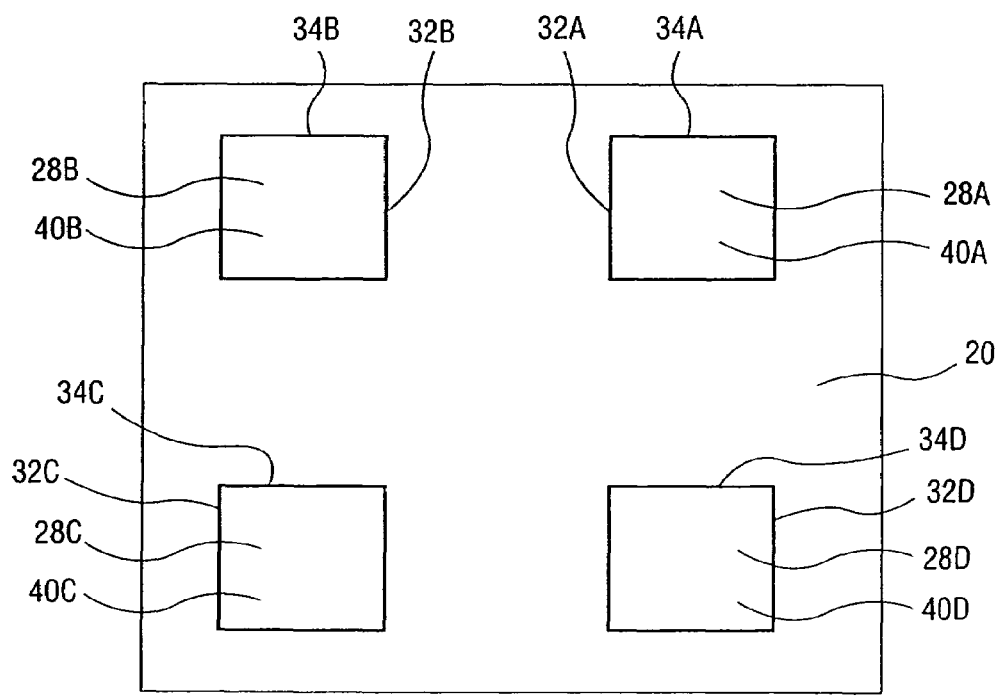

Referring now to FIGS. 2A and 2B, alternate embodiments of the calibration and alignment fixture 20 for the scanning beam delivery system having eye tracking cameras are illustrated. In FIG. 2A, a plurality of cross-like openings 28A–28D and reference-edges 32A–32D, 34A–34D are formed in the fixture 20 to allow for laser energy and laser beam shape calibrations. Openings 28A–28D may also function as alignment pupils 40A–40D for the eye tracking cameras. FIG. 2B shows a plurality of square openings 28A–28D and reference-edges 32A–32D, 34A–34D formed in the fixture 20 to allow for laser energy and laser beam shape calibrations. Square openings 28A–28D may also function as alignment pupils 40A–40D for the eye tracking cameras.

Figure 3:
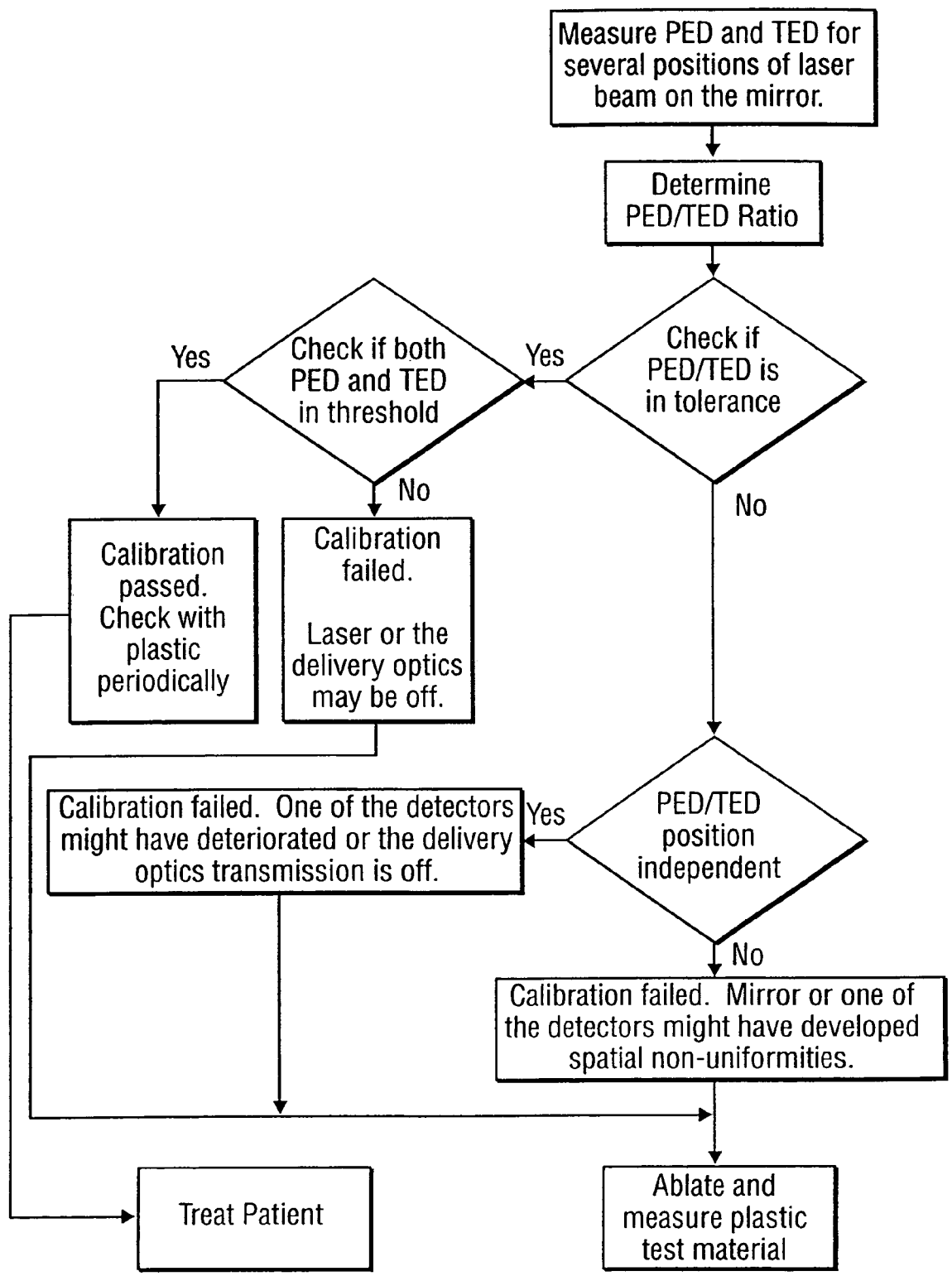
FIG. 3 is a simplified block diagram illustrating a method for calibrating laser energy from a laser beam delivery system employing the system of FIG. 1.

Referring now to FIG. 3, laser energy calibration is performed by utilizing measurements from the two energy detectors 18 and 22. The first photodetector 18 is placed behind the mirror 14 that directs the laser beam 16 to a treatment plane, and typically to the patient's eye. The first photodetector 18 measures the leakage of ultraviolet laser through the mirror 14 and may be referred to herein as the patient energy detector (PED). The second photodetector 22 is placed adjacent the calibration fixture 20 and it measures the pulse laser energy used for a given treatment procedure. This photodetector may be referred to herein as the treatment energy detector (TED). The mechanical fixture 20, as described above, is placed adjacent the treatment plane and is positioned relative to the beam delivery system 12 via a hinged support arm or mechanism 21 that allows movement of the fixture in and out of the treatment plane. The TED is placed behind the calibration fixture 20. The fixture 20 has opening 28 through which the whole of laser beam 16 can pass through while the laser beam position is scanned over a specified area.

In operation, laser energy calibration comprises the steps of transmitting the laser beam 16 suitable for ablation of corneal tissue from the mirror 14, scanning the laser beam 16 through the opening 28 in the fixture 20, and measuring the output signals of the first 18 and second 22 photodetectors during the scanning. The first photodetector measures the laser energy leakage through the mirror. The second photodetector measures the laser light energy passing through the fixture opening. A calibration of the system is determined by comparing the energy measurements.

Multiple output signal measurements from the first 18 and second 22 photodetectors are generated as the laser beam is transmitted from several different positions on the fixed mirror 14 by moving the laser beam 16 in a direction designated by reference number 42 (FIG. 1). Typically, the laser beam delivery system 12 will include scanning optics for moving the laser beam 16 along a predetermined pathway. In some instances, the mirror 14 may be attached to a gimbal so that the rotating mirror may scan the laser beam across the calibration fixture. The laser beam 16 will typically be oriented perpendicular to the second photodetector 22 as the laser beam 16 is directed across the calibration fixture 20. A large number of measurements are made so that contributions due to detector noise are relatively insignificant as compared to an average of laser energy pulse measurements.

The computer system 30 records, processes, and analyzes the output signals 24 and 26 emitted from the first and second photodetectors 18 and 22. An exemplary protocol for calibrating laser energy is depicted in block diagram fashion in FIG. 3. PED 18 and TED 22 values are measured at several positions of the laser beam 16 on the mirror 14. The ratio of output measurements, PED/TED, is then determined and the PED/TED ratio is then compared against a predetermined tolerance. If the ratio is within the predetermined tolerance, the output measurement from the PED is independently compared against a first threshold range and the output measurement from the TED is independently compared against a second threshold range. If the output measurement from the PED is within the first threshold range and the output measurement from the TED is within the second threshold range, the calibration fixture 20 is removed from the treatment plane and the laser beam 16 directed towards a patient's cornea for a sculpting treatment as the laser energy measurement is accurately calibrated.

However, if the output measurement from the PED is outside the first threshold range or the output measurement from the TED is outside the second threshold range, a fault is indicated in the laser beam delivery system 12, such as flawed delivery system optics or a flawed laser. Moreover, in the case where the PED/TED ratio is outside the predetermined tolerance, each PED/TED ratio of the output measurements from the first and second photodetectors is analyzed for each laser beam position scanned on the mirror to check if the PED/TED ratio was position independent. If the PED/TED ratio is not position independent, a fault is indicated either in the mirror 14, PED 18, or TED 22. If the PED/TED ratio is position independent, a fault is indicated either in the TED 18, PED 22, or laser beam delivery system 12. For example, one of the photodetectors may have deteriorated or the delivery optics transmission is off. Moreover, in all failed calibration scenarios described above, an ablation test on plastic test material may be further performed.

A variation in each photodetector 18, 22 due to spatial non-uniformity is measured prior to laser beam scanning with the calibration fixture to separate this effect from the laser energy calibration analysis described above. In particular, spatial non-uniformity may be measured by scanning the laser beam over the two detectors, PED and TED, without the fixture 20 to obtain a map of the PED/TED ratio over the two dimensional range of laser beam positions during scanning. For example, the laser beam may be scanned in 0.1 mm increments over a circular area having a diameter of approximately 10 mm. This sampling provides about 8000 measurements of the PED/TED ratio and forms a PED/TED map. The tolerance and threshold values will depend on the level of calibration accuracy desired. For example, the predetermined ratio tolerance provides preferably 8% or less inaccuracy, more preferably 4% or less inaccuracy, most preferably 2% or less inaccuracy while the first and second threshold values may provide 1% or less inaccuracy. The present calibration methods advantageously allow for enhanced laser calibration as measurements from two photodetectors 18 and 22 are used to determine laser calibration accuracy. Moreover, measurements from two photodetectors allows for fault detection within the laser delivery system to be narrowed down to a specific component(s) of the system, which in turn facilitates fast and accurate adjustment of the laser system 10.

Figure 4:
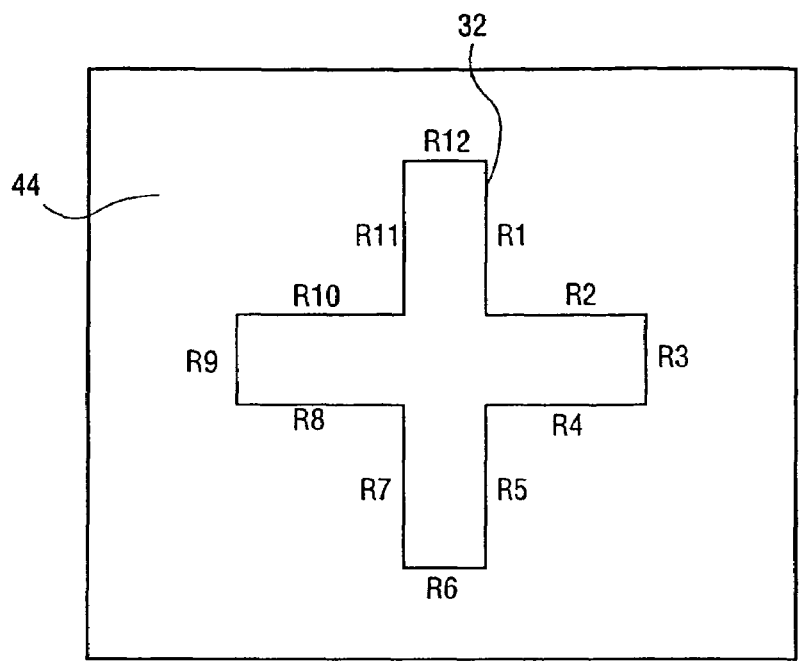
FIG. 4 illustrates another configuration of a calibration fixture which may be employed in the system of FIG. 1.
Figure 5:
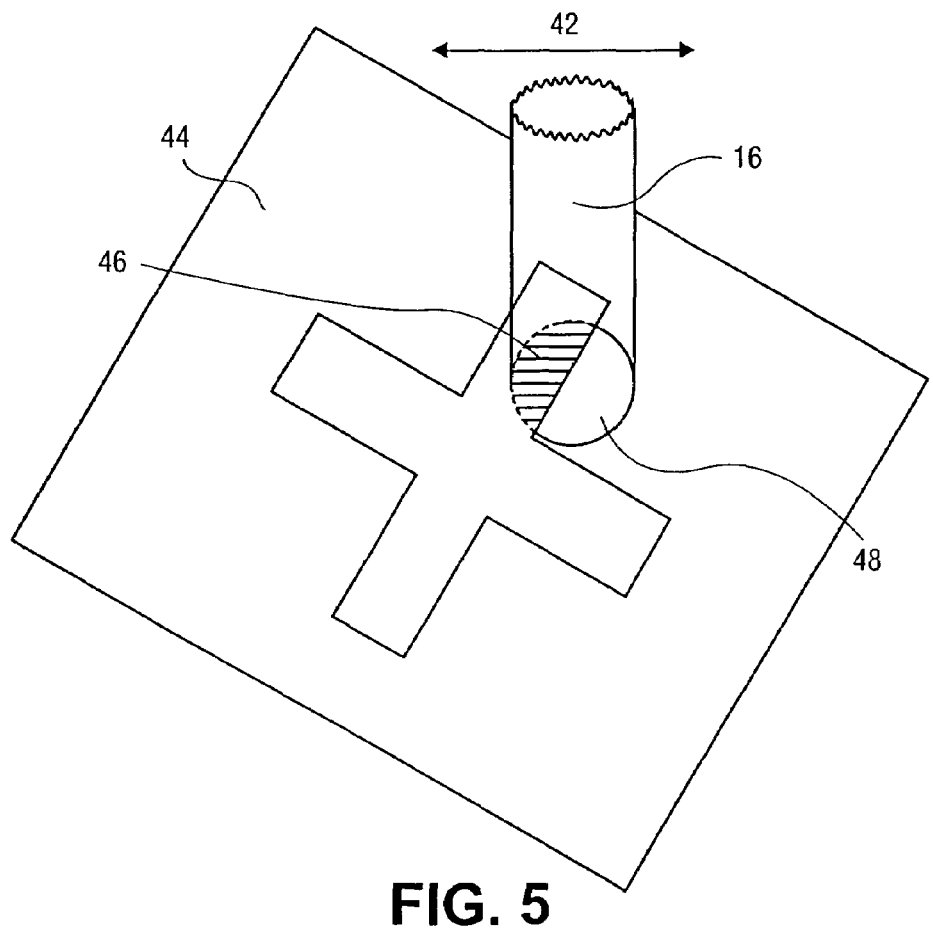
FIG. 5 is a perspective view of a laser beam being scanned over a reference-edge of the calibration fixture of FIG. 4 at a moment in time when the laser beam is centered over the reference-edge.

Referring now to FIG. 4, another configuration of a calibration fixture 44 is illustrated. Such a fixture may be utilized for laser energy measurement as well measuring laser beam shape and dimensions with the system of FIG. 1. FIG. 5 shows a perspective view of the laser beam 16 which is directed downwardly towards the first reference-edge 32, with the second photodetector 22 positioned therebehind (not shown), at a moment in time during the laser beam scanning when a center of the laser beam 16 is positioned exactly at the edge of the first reference-edge 32. The laser beam 16 is typically directed from the mirror 14 across the first reference-edge 32 so that the output signal from the second photodetector 22 corresponds to an area of the laser beam incident on the second photodetector (i.e. the part of the laser beam that is not blocked by the reference-edge 32) during the scanning. As illustrated in FIG. 5, in the case where the laser beam 16 has a circular shape, a first half 46 of the laser beam 16 will be incident on the second photodetector 22 while a second half 48 of the laser beam 16 will be occluded by the calibration fixture 20.

Figure 6A:
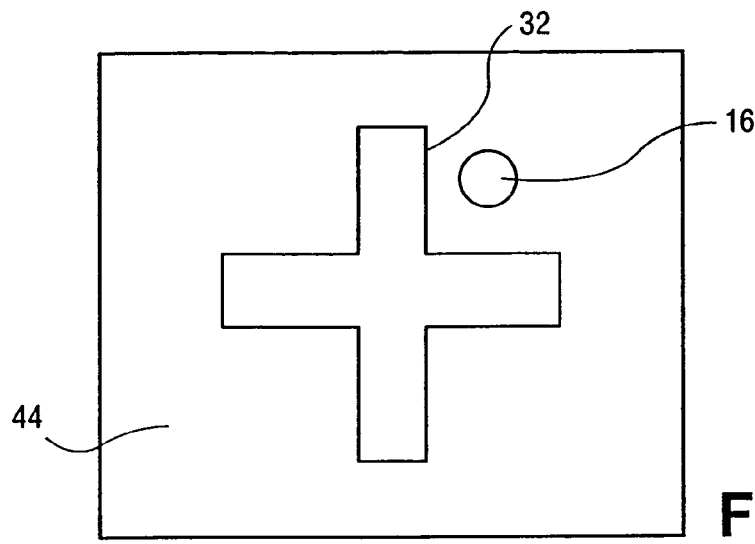
FIGS. 6A–6C are sequential illustrations of the laser beam moving across the reference-edge of FIG. 4.
Figure 6B:
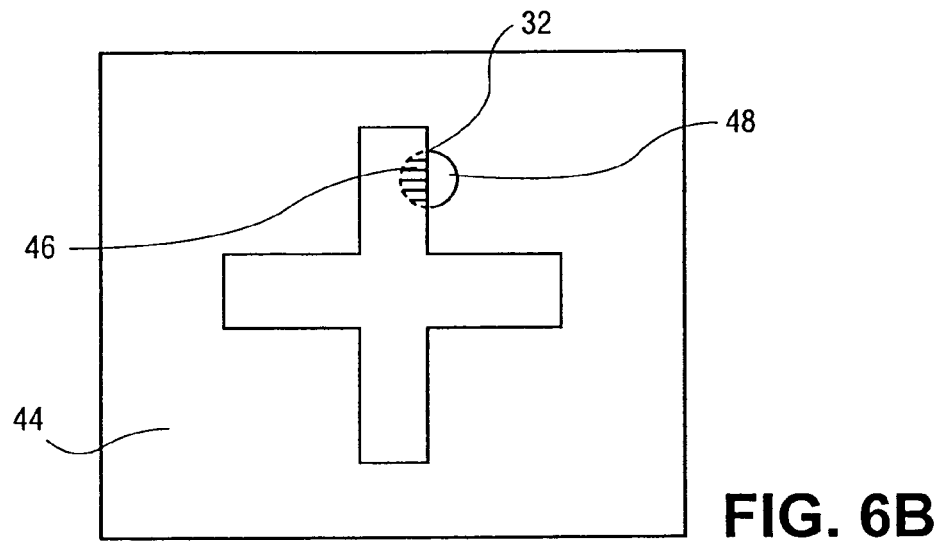
Figure 6C:
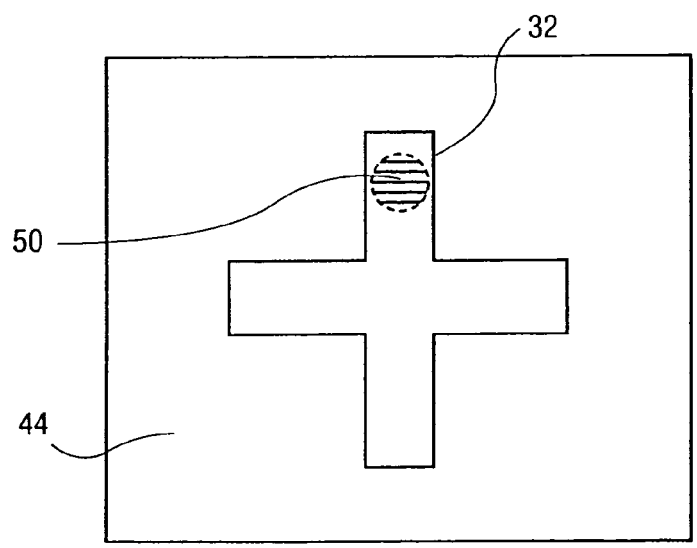

Referring now to FIGS. 6A through 6C, sequential movement of the laser beam 16 during scanning across the first reference-edge and onto the second photodetector 22 is illustrated. Multiple output signal measurements are generated from the second photodetector 22 as the laser beam 16 is fully incident on the calibration fixture 20 (i.e. the laser beam is fully blocked from reaching the photodetector by the reference-edge), as shown in FIG. 6A, to the laser beam 16 being fully incident (as denoted by reference numeral 50) on the second photodetector 22, as shown in FIG. 6C. FIG. 6B shows a first half 46 of the laser beam 16 incident on the second photodetector 22 while a second half 48 of the laser beam 16 is incident on the calibration fixture 20. An average of multiple output signal readings reduces variations in the data due to photodetector noise. By measuring the output of the second photodetector it is possible to determine intensity profile, dimensions, and shape of the laser beam during the scanning. By comparing the measured energy signal of the second photodetector 22 to the first energy detector 18, variations in the energy emitted by each pulse of the laser 11 are rejected as common mode noise.

Figure 7:
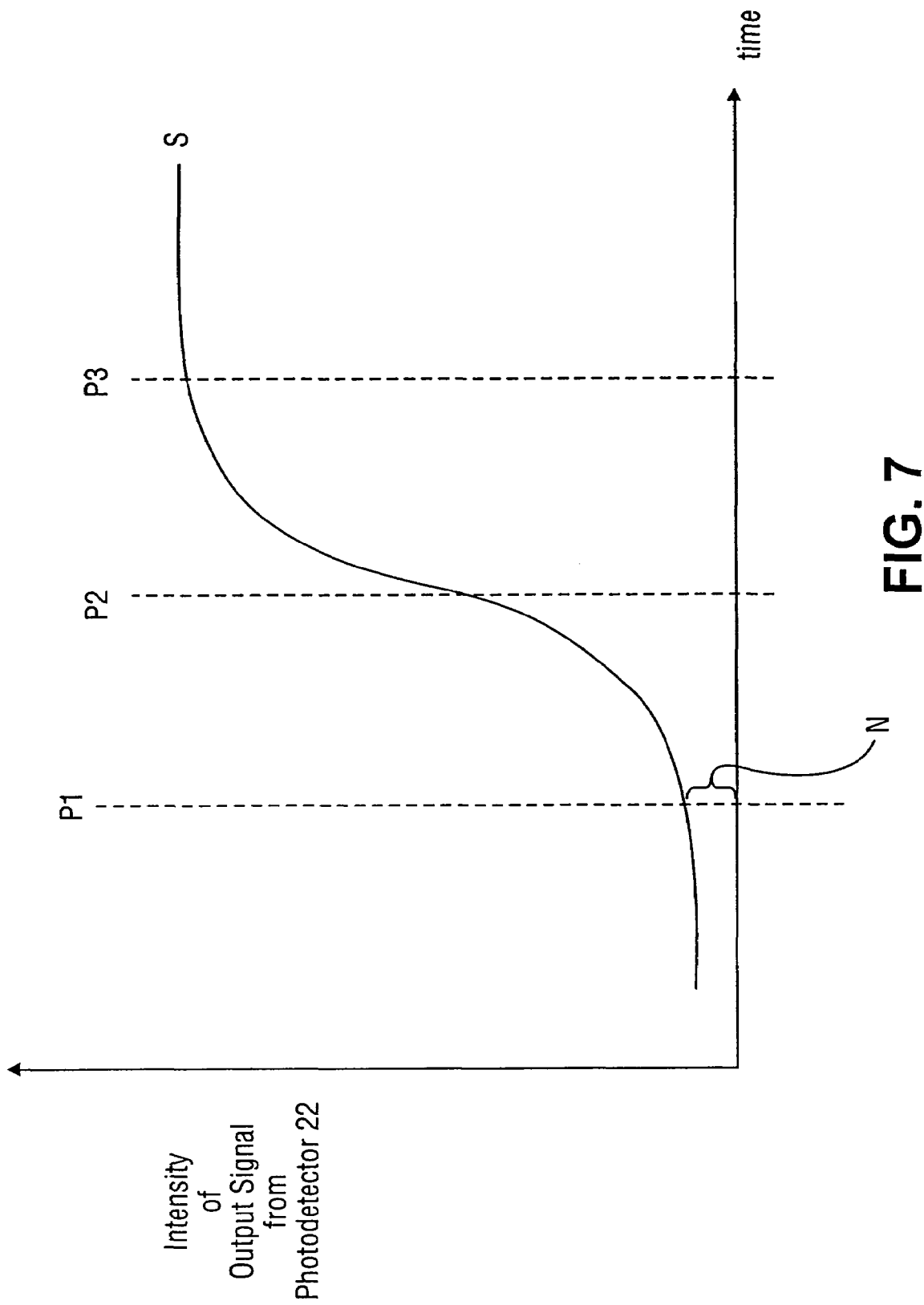
FIG. 7 graphically illustrates output signals of the second photodetector during the scanning illustrated in FIGS. 6A–6C.

Referring now to FIG. 7, an intensity profile of the laser beam 16 may be determined from the output signal S from the second photodetector 22 taken over time during the scanning (FIGS. 6A–6C) of the laser beam 16 across the first reference-edge 32 and onto photodetector 22. The intensity of output signal S of the second photodetector 22 will correspond to energy in the area of laser beam 16 which is not blocked along the first reference-edge 32 of calibration fixture 20 and is therefore directly incident on second photodetector. Specifically, the intensity of signal S can be represented as an integral of the laser beam profile which is not blocked by the reference-edge. Such integrals for a Gaussian pulse can be represented as follows:

$S = S_0 \int^x$(laser beam intensity profile in 1D)$dx$ or $S = S_0 \int^{surface}$(laser beam intensity profile in 2D)$d$(surface)

or for a "top hat" pulse of amplitude A and diameter $X_o$ in which the energy distribution is substantially uniform across the cross-section of the pulse, as follows:

$$S = 2AS_0^x \int \sqrt{\left(\frac{x_0}{2}\right)^2 - \left(x - \frac{x_0}{2}\right)^2} \, dx$$

Points P1, P2, and P3 in FIG. 7 illustrate the measured intensity of output signal S corresponding to the integrated laser beam profile at the moments in time when laser beam is positioned as shown in FIGS. 6A, 6B, and 6C respectively. When laser beam 16 is positioned to be fully occluded by calibration fixture 20, the photodetector 22 will typically emit only a small signal intensity N, representing noise in the system. As laser beam 16 is scanned across the first reference-edge 32, progressively more of the area of the laser beam 16 will reach the second photodetector 22, increasing the intensity of the second photodetector's output signal S. When laser beam 16 reaches the position illustrated in FIGS. 5 and 6B, such that the first half 22 of beam spot 20 will be incident upon the photodetector, signal S will reach approximately ½ of its maximum signal intensity at point P2. Finally, when laser beam 16 eventually reaches the position illustrated in FIG. 6C, such that the entire laser beam 16 is incident upon photodetector 22, signal S will reach its maximum signal intensity at point P3. Hence, for a generally circular laser beam 16, the intensity of output signal S will be in the shape of an S-shaped curve as shown in FIG. 7. In an exemplary embodiment, the signal 26 measured by detector 22 is divided by the signal 24 from detector 18 to reject common mode noise from pulse to pulse energy variations in the laser beam 16 emitted from laser 11. This divided signal is preferably normalized and plotted as shown in FIG. 7. The laser beam intensity profile is then determined from an s-shaped curve of the normalized values.

Dimensions of the laser beam may then be determined from the laser beam intensity profile. A shape of the laser beam 16 may further be determined by measuring a rate of change of the output signal S from the second photodetector 22 during scanning. Laser beam shape and dimension measurements provide information on beam quality, such as ellipticity, eccentricities, and asymmetries in the laser beam.

Figure 8:
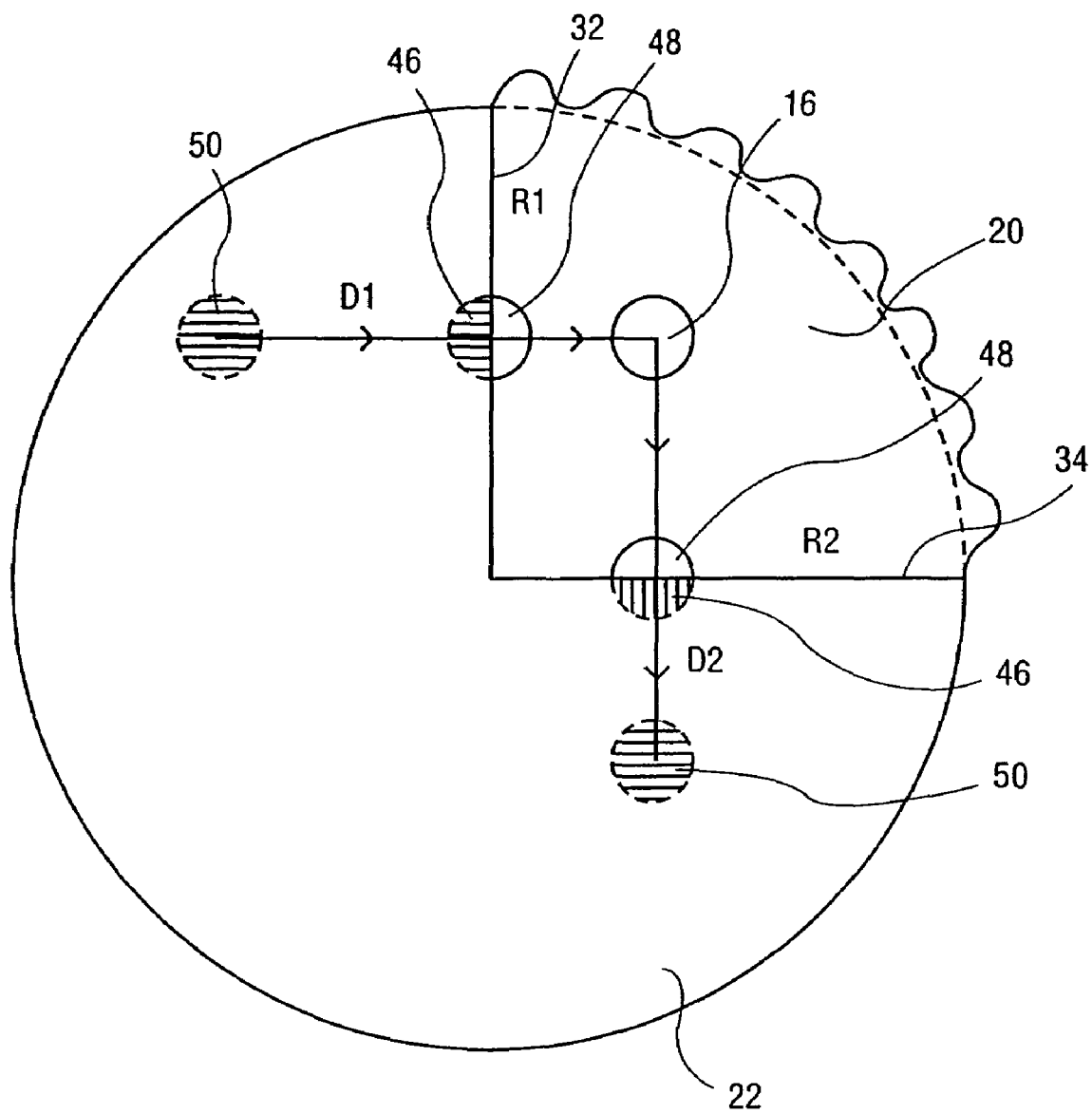
FIG. 8 is a top plan view of a laser beam being scanned over two perpendicular reference-edges of the calibration fixture of FIG. 4.

Referring now to FIG. 8, a preferred method for determining dimensions, shape, intensity, and position of the laser beam is illustrated. The method comprises scanning the laser beam 16 in a first direction D1 across the first reference-edge 32 followed by scanning the laser beam in a second direction D2 across the second reference-edge 34 oriented at an angle to the first reference-edge 32, wherein the photodetector 22 is positioned behind the first and second reference-edges 32 and 34. An output signal from the photodetector 22 is measured during the scanning, the output signal corresponding to an area of the laser beam 16 incident on the photodetector 22 during the scanning. Preferably, a signal from photodetector 18 is measured to reject common mode noise as described above. Scanning along two orthogonal directions allows for two dimensional measurements which in turn enhances laser beam dimension and shape measurements. A characteristic of the laser beam may be derived from the laser beam energy measured by the photodetector.

One analysis method is to compute first four moments of the laser beam intensity profiles projected along the two orthogonal axes D1 and D2. As mentioned above, the reference-edge setup provides integration of these intensity profiles. Mathematically the moments of the beam intensity profiles can be calculated using the integrated profile. For example, the measured moments may be compared against moments of ideal Gaussian distribution. The difference between the two provides information about the beam quality, such as laser beam diameter and/or shape.

Figure 9:
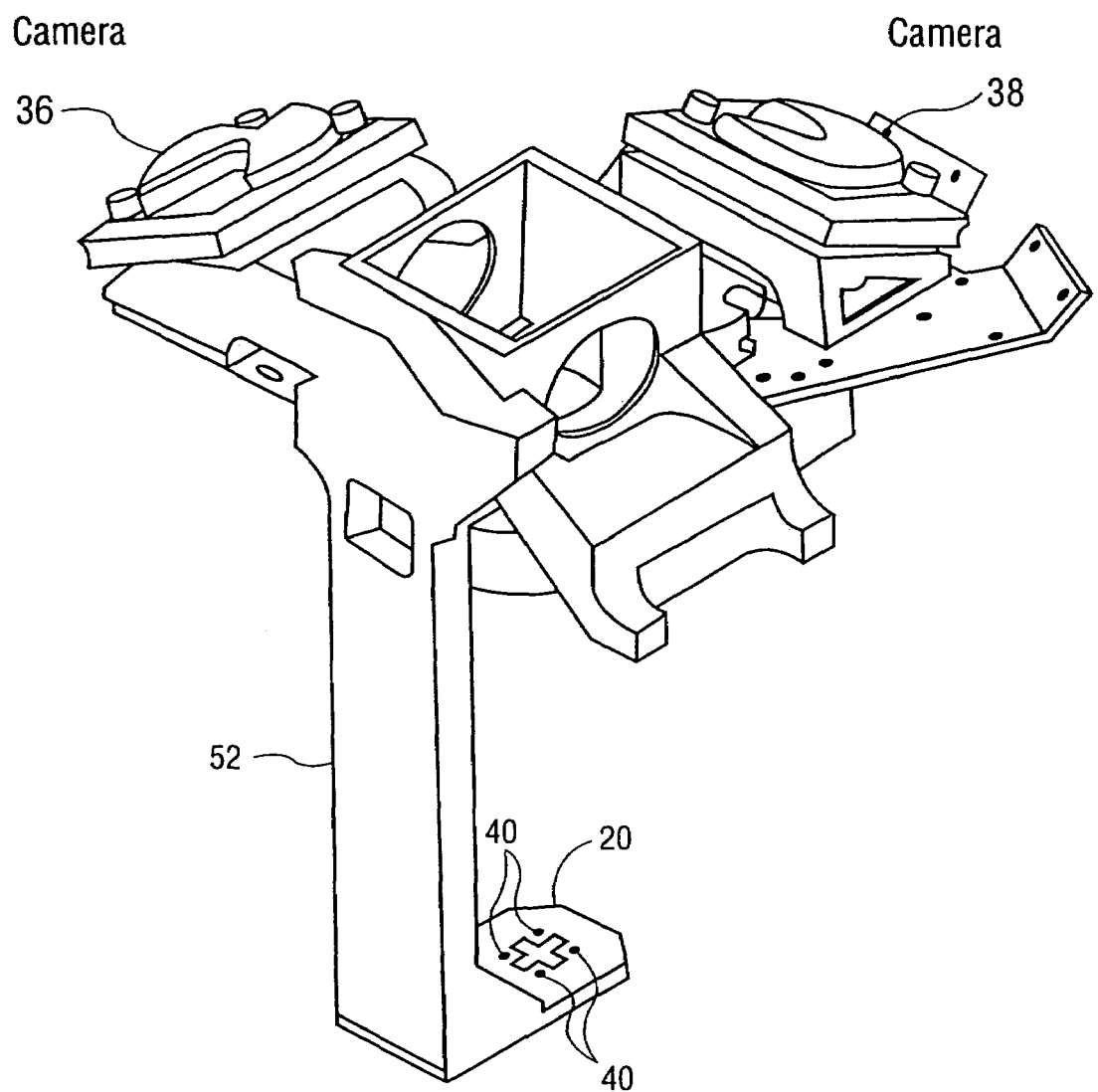
FIG. 9 is a simplified perspective view of eye tracking cameras in conjunction with the calibration and alignment fixture of FIGS. 1 and 2.

Referring now to FIG. 9, the fixture 20 may further allow alignment of the horizontal and vertical eye tracker cameras 36 and 38, so as to zero x and y positions provided by the cameras, and so as to orient the cameras properly about their optical axes. A structure 52 holds the fixture 20 at the desired position during calibration. To provide adjustability, the cameras are mounted so as to have three axes of rotation. Adjustments about these axes will preferably be provided by fine screw adjustment mechanisms with lock-downs provided to secure the position of the camera once at the desired position and orientation.

Exemplary eye tracker cameras 36, 38 for laser eye surgery are described in U.S. Pat. No. 6,322,216 B1, assigned to the assignee of the present application, the full disclosure of which is incorporated herein by reference. Generally, first and second cameras or image capture devices are oriented toward the eye. The energy delivery system laterally deflects the energy stream toward the corneal tissue along a first and second axis in response to movement of the eye sensed by the first and second image capture devices. The horizontal and vertical cameras will often comprise commercially available tracking systems such as those available from Iscan, Inc. of Burlington, Mass., or other comparable systems.

The fixture 20 will have a pattern on a surface thereof comprising four dark circles 40 that emulate eye pupils disposed at four corners of a square. The dark circles 40 may be imaged by the eye tracking cameras 36 and 38 so as to align the image capture devices with the laser system. Typically, an electronic cross-hair serves as the camera's reference. The electronic cross-hair is aligned both rotationally and in the x,y planes with the fixture 20. The dark circles 40 are used for scale calibration. The dark circles 40 are 14 mm apart. The eye tracker camera locates the dark circles 40 and measures the number of pixels between the circles. The scale factor is 14 mm/number of pixels (mm/pixel). The dark circles can be used to confirm the optical center and rotational alignment of the cameras.

Figure 10:
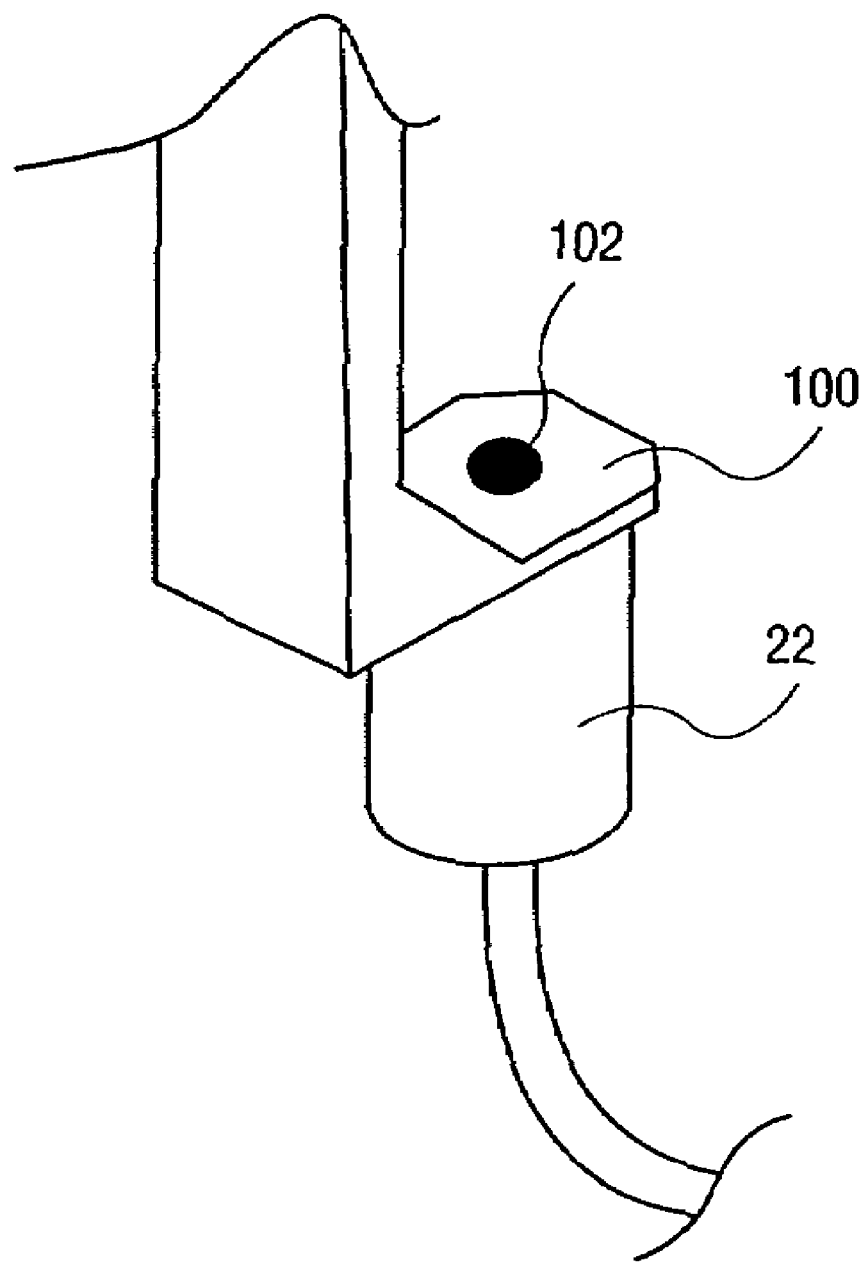
FIGS. 10 and 11 illustrate an alternate embodiment of the calibration and alignment fixture which may be employed in the system of FIG. 1.
Figure 11:
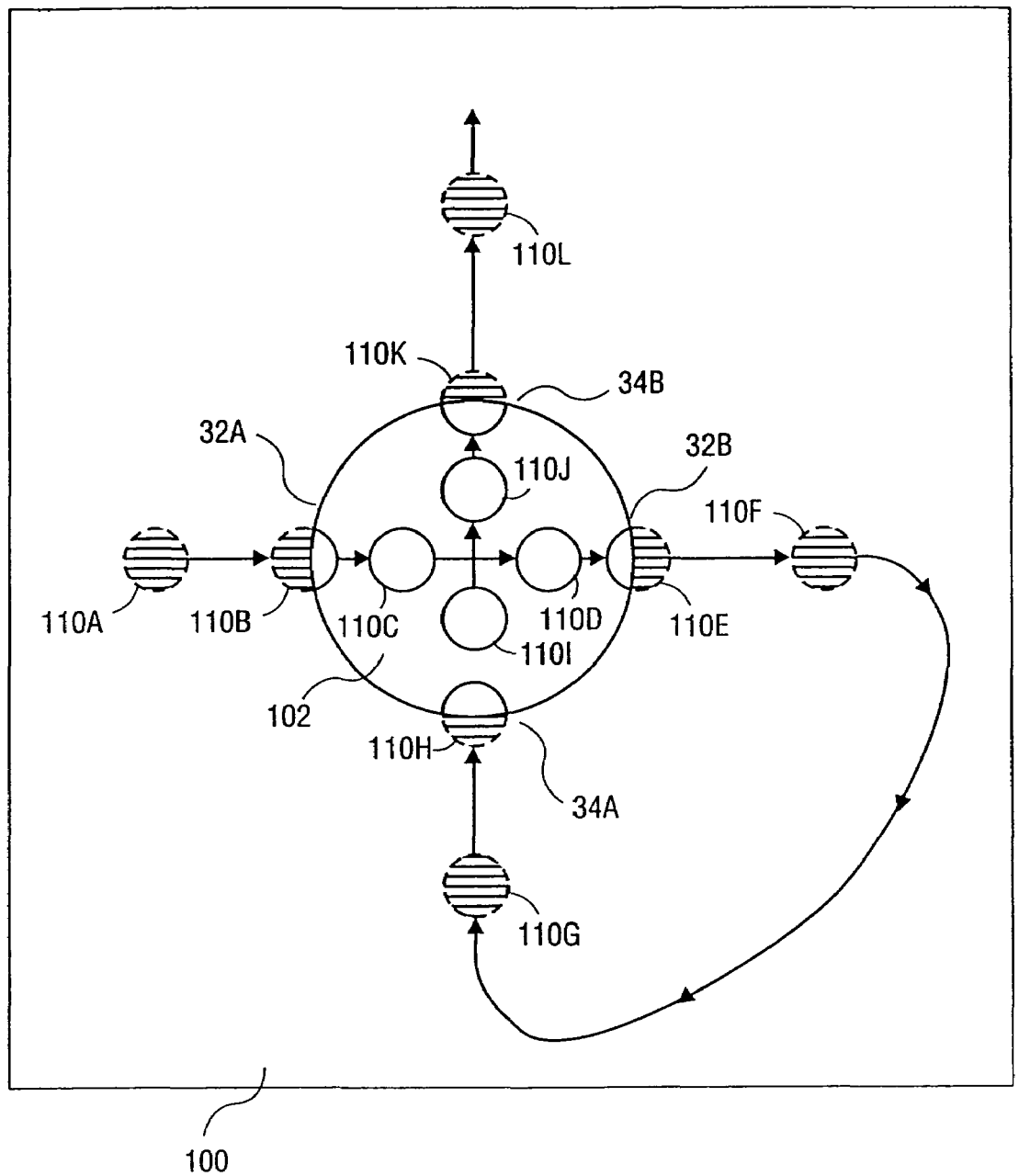

Referring now to FIGS. 10 and 11, an alternate embodiment of calibration fixture 100 for use with an eye tracking and laser system employs a single aperture 102 formed in the fixture 100. The fixture 100 is formed from a material that does not transmit the laser beam. The aperture 102 emulates a pupil of an eye and has a diameter in the range from about 2 mm to 12 mm, preferably from about 3 mm to 9 mm, and more preferably from about 4 mm to 8 mm. Alternatively, the aperture 102 may emulate another structure of an eye, for example a limbus of the eye. A photodetector 22 measures the laser beam energy passing through the aperture 102 as the laser beam scans across the fixture 100. The laser beam profile is measured as illustrated in FIG. 11. The position of laser beam 16 is scanned over aperture 102. Aperture 102 includes vertical reference-edges 32A and 32B that are approximately perpendicular to horizontal reference-edges 34A and 34B. Alternatively, non-perpendicular reference edges may be used. Laser beam positions 110A to 110L include positions intended to fully block and fully transmit laser beam 16. The laser beam intensity profile may be determined from the signal output of the photodetector 22 during scanning across positions 110A to 110L. Also, the laser beam profile may be calculated by comparing measured energy levels to expected energy levels for the laser beam blocked by slightly curved reference-edges 32A, 32B, 34A and 34B. Opening 102 may alternatively function as an alignment pupil or limbus for the eye tracking cameras.

Figure 12:
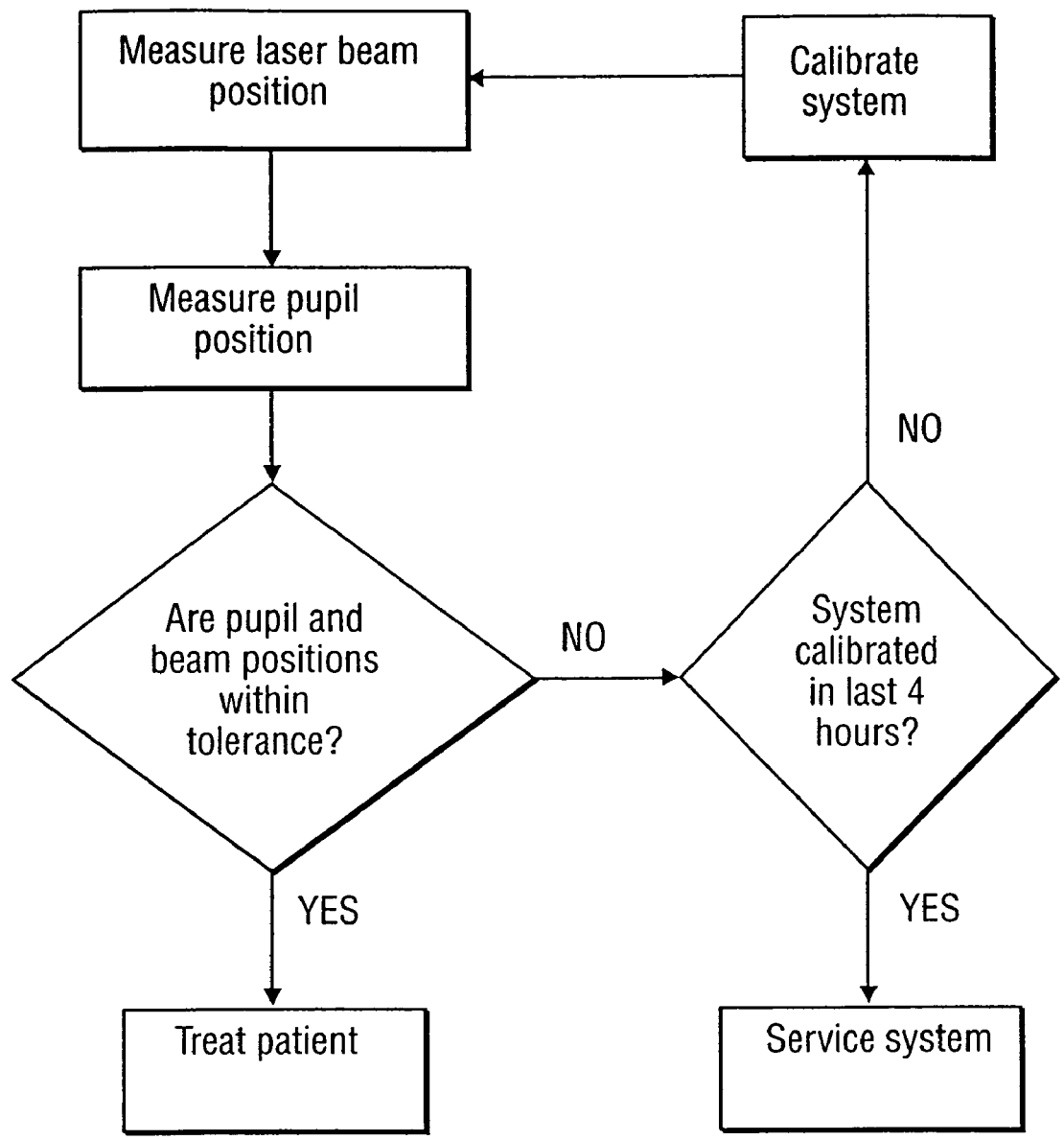
FIG. 12 is a simplified block diagram illustrating a method for calibrating a laser eye surgery system having eye tracking cameras.

Referring now to FIG. 12, a preferred method of testing alignment of a laser beam system and eye tracking system is illustrated. A laser beam position is measured from the reference-edge setup described above. Alternatively, the laser beam position may be measured as described in U.S. Pat. No. 5,928,221, the full disclosure of which is incorporated herein by reference. The measured laser beam position is stored in the memory of computer 30. The position of an artificial pupil is measured as described above. Alternatively, a position of another artificial structure that is optically similar to another structure of an eye, such as a limbus, may be measured. For example, in the case of contrast tracking of the limbus, the artificial structure comprises a contrast boundary optically similar to at least a portion of a limbal boundary formed between a scleral tissue structure and a corneal tissue structure. The measured artificial eye structure position is stored in a memory of computer 30. The measurement of the artificial eye structure and laser beam may be sequential and include different calibration targets for measuring the artificial eye structure and measuring the laser beam. The measured position of the artificial eye structure is compared to the measured position of the laser beam. If the measured positions of the artificial eye structure and laser beam are within a predetermined threshold amount, for example 0.1 mm, a patient is treated. If the measured positions of the artificial eye structure and laser beam are greater than a threshold amount, the system is calibrated if it has not been calibrated in the last 4 hours. The comparison of the measured artificial eye structure and measured laser beam positions is repeated in response to the system not having been calibrated within 4 hours. If the system has been calibrated within the last 4 hours, the system is serviced.

In another preferred aspect, tools can be used to align the targeting optics of the laser delivery system. Specifically, after locating a center of laser beam the spot as it is scanned across a photodetector, the beam delivery system (including galvanometers) can be precisely aligned to compensate for any difference between the position of the laser beam as determined by the targeting optics, and that indicated by the tool. A suitable material for a tool which fluoresces but does not ablate is preferred. Such material may comprise a white stock paper or a white business card. Also, a suitable fluorescent plate material which can be purchased from Startech Inc, of Connecticut can be used.

Figure 13:
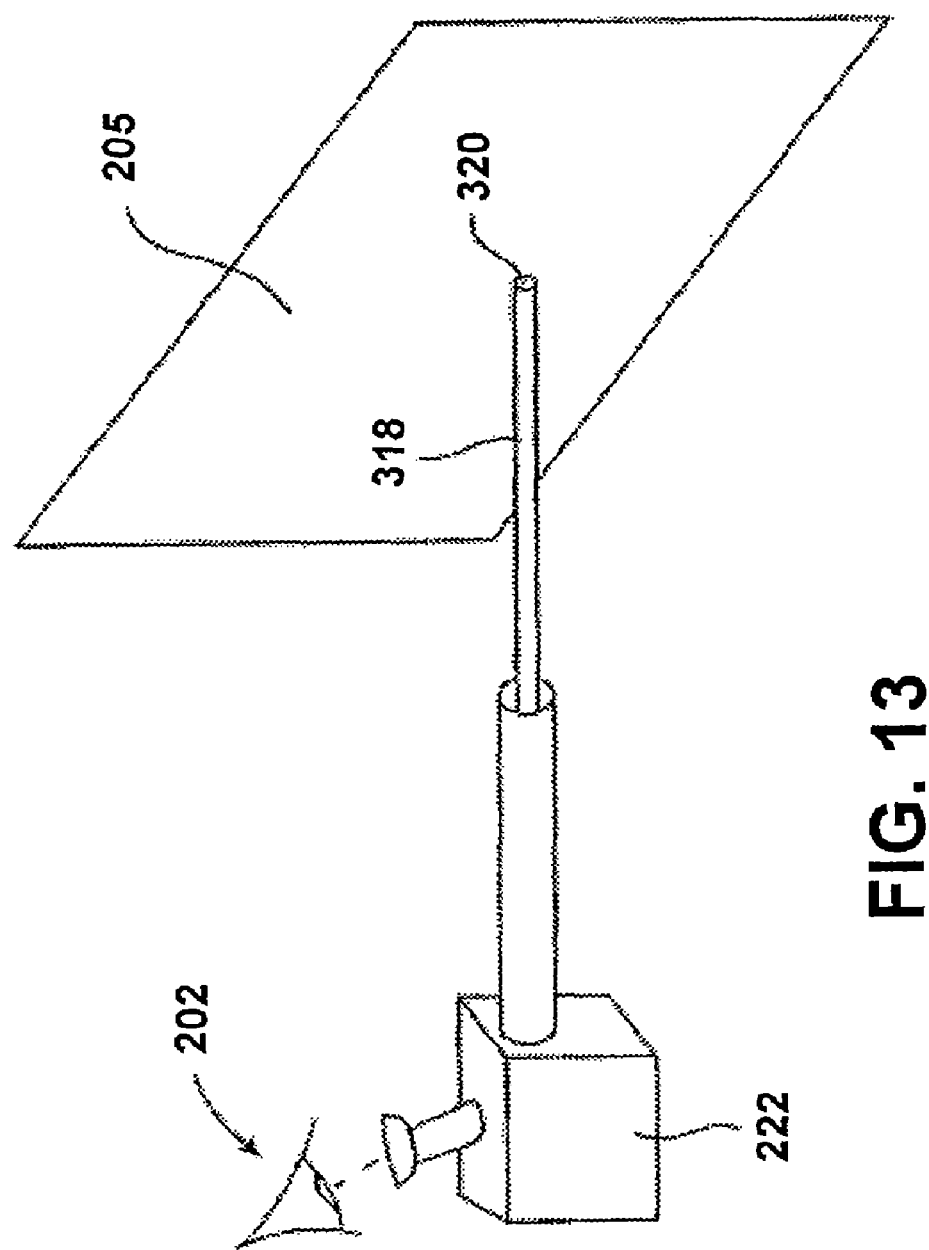
FIG. 13 is a perspective view of the laser beam delivery system directing a laser beam at a screen which fluoresces in the region where the laser beam is incident thereon.
Figure 15:
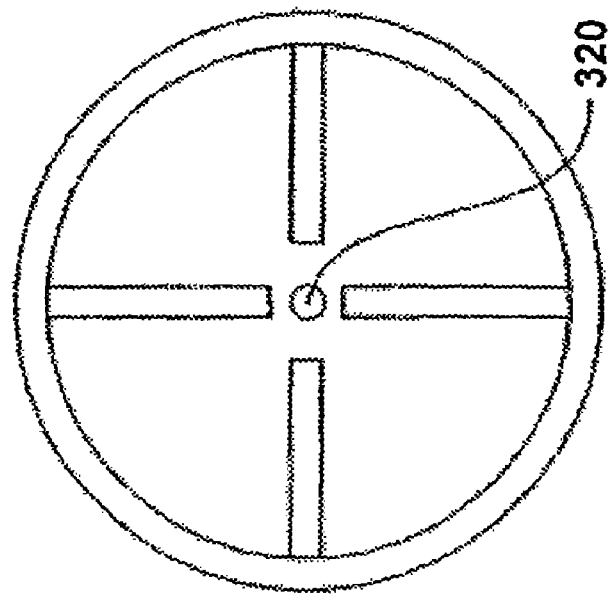
FIG. 15 is a view corresponding to FIG. 14, after system calibration.
Figure 14:
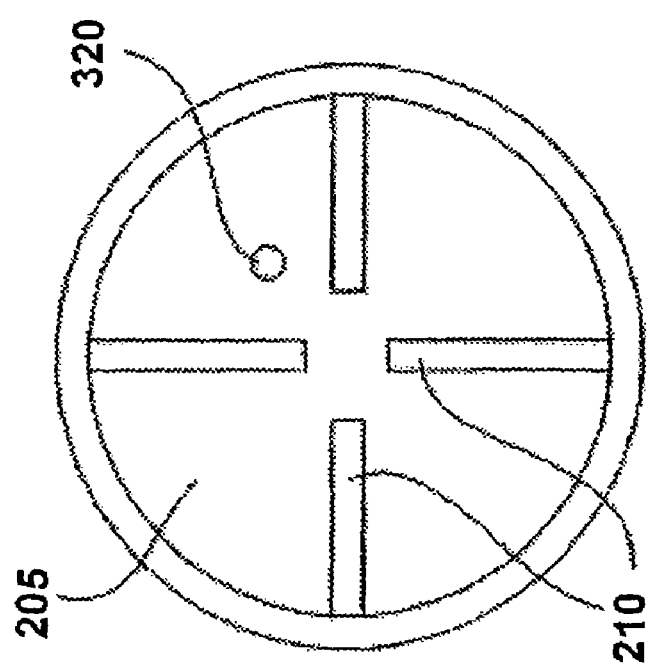
FIG. 14 is a view through the targeting optics of the laser beam delivery system prior to system calibration when the laser beam is directed to the fluorescing screen of FIG. 13.

In another embodiment, a measurement/alignment tool comprises a screen 205 which fluoresces in response to laser light incident thereon, as illustrated in FIGS. 13 to 15. Referring to FIG. 13, laser beam 318 is directed incident to screen 205, causing screen 205 to fluoresce in the region of beam spot 320. An operator 202 looking through targeting optics 222, (which preferably comprises a system microscope), views fluorescing of beam spot 320, as shown in FIG. 14. Targeting optics 222 displays a reticle 210 to operator 202, and the operator adjusts the laser beam delivery optics so that the fluorescing beam spot is aligned with the reticle.

Advantageously, adjusting the location of beam spot 320 can be effected using the beam scanning mechanism. This may significantly facilitate alignment, as the system microscope need not be moved with a precise X-Y adjustment mechanism. Instead, the targeting signals transmitted to the galvanometric laser beam delivery optics can be selectively altered or offset to aim the beam at the target location. Scanned accuracy may be enhanced by moving the beam between a plurality of target locations, and by individual beam shot targets using the signal offsets throughout the resculpting procedure. In alternative embodiments, the beam delivery optics may be mechanically adjusted to move beam spot 320 between the cross-hairs of reticle 210, thereby aligning the targeting optics of the laser beam delivery system.

In some embodiments, the tool may be removably positioned at or near the location which will be occupied by the eye during refractive resculpting. The tool may be held by a swing-away arm or the like in a conventional manner. To set or check the system prior to a resculpting procedure, the operator enters an alignment mode. In this mode, reticle 210 remains stationary, and the laser fires to induce fluorescence at beam spot 320. The beam spot may be moved by the operator via an input device such as a joystick, mouse, switches, or the like which adjusts the beam delivery optics by changing the signal sent to the galvanometers. The laser beam would again fire producing a new laser spot 320, and the operator would continue to adjust the signal offsets until the laser beam is coincident with the laser beam. When coincidence is achieved, the operator can press a button (or provide any alternative signal to the system) and the system computer will then store the offset signals for determining the ablation center. Typically, the reticle will also be used to align the eye with the system after the tool is moved out of the way.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A laser beam delivery calibration system, comprising:
    a laser for generating a corneal ablation laser beam;
    a target which is adapted to fluoresce when the laser beam is incident thereon;
    a laser beam targeting system for directing the laser beam towards, and scanning the laser beam relative to, the target;

targeting optics for imaging the target when the target fluoresces in response to the laser beam incident thereon, the targeting optics defining a target position; and an adjustment mechanism for aligning the laser beam targeting system with the target position.

2. The system of claim 1, wherein,
the targeting optics comprises a reticle.

3. The system of claim 1, wherein the targeting optics for viewing the position of the target comprise a microscope.

4. The system of claim 1, wherein the laser beam targeting system is configured to scan the laser beam across the target in response to target signals, and wherein the adjustment mechanism alters the target signals so as to align the target position with the targeting optics.

5. The system of claim 4, wherein the adjustment mechanism is configured to alter the target signals using an offset between the target position and a laser beam spot location.

6. The system of claim 5, wherein the laser beam targeting system comprises galvanometers, and wherein the adjustment mechanisms alters the target signals sent to the galvanometers per the offset.

7. The system of claim 1, wherein the adjustment mechanism is configured to alter the target signals using a plurality of offsets between a plurality of target positions and laser beam spot locations throughout a corneal rescuipting procedure.

8. The system of claim 1, where the adjustment mechanism comprises a mechanical adjustment mechanism to move optics of the laser beam delivery system.

9. The system of claim 1, wherein the system has a resculpting mode and an alignment mode, the system in the resculpting mode configured to resculpt a cornea of a patient while the cornea is disposed at a treatment location, the system in the alignment mode having the target removably positioned at or near the treatment location.

10. The system of claim 9, further comprising an input device, the laser beam targeting system moving the laser beam and an associated laser beam spot location relative to the target in response to adjustment commands entered via the input device when the system is in the alignment mode.

11. The system of claim 9, wherein the system is configured to store an offset of the laser beam targeting system in the alignment mode, and wherein the system is configured to use the offset during corneal resculpting when in the resculpting mode.

* * * * *